(12) United States Patent
Lee et al.

(10) Patent No.: US 10,025,098 B2
(45) Date of Patent: Jul. 17, 2018

(54) ELECTRONIC GLASSES AND METHOD FOR CORRECTING COLOR BLINDNESS

(71) Applicant: Samsung Electronics Co., Ltd., Gyeonggi-do (KR)

(72) Inventors: Jaewook Lee, Gyeonggi-do (KR); Anki Cho, Gyeonggi-do (KR); Juyeon Seo, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/582,723

(22) Filed: Dec. 24, 2014

(65) Prior Publication Data

US 2015/0192776 A1 Jul. 9, 2015

(30) Foreign Application Priority Data

Jan. 6, 2014 (KR) ........................ 10-2014-0001457

(51) Int. Cl.
| | |
|---|---|
| *G09G 5/00* | (2006.01) |
| *G02B 27/01* | (2006.01) |
| *G06F 3/0487* | (2013.01) |
| *G09B 21/00* | (2006.01) |
| *A61B 3/06* | (2006.01) |
| *G09G 3/20* | (2006.01) |

(52) U.S. Cl.
CPC .......... *G02B 27/0172* (2013.01); *A61B 3/066* (2013.01); *G02B 27/0101* (2013.01); *G06F 3/0487* (2013.01); *G09B 21/008* (2013.01); *G09G 3/2003* (2013.01); *G02B 2027/014* (2013.01); *G02B 2027/0112* (2013.01); *G02B 2027/0178* (2013.01); *G09G 2320/0242* (2013.01); *G09G 2320/0666* (2013.01)

(58) Field of Classification Search
CPC .... G02B 2027/0134; G02B 2027/0141; G02B 2027/0147; G02B 27/017; G02B 2027/0178; G02B 27/021; G02B 27/022; G02B 27/04; G02B 27/06; G02B 27/02; G02B 27/08; G02B 27/026
USPC .................................................. 345/7–8, 690
See application file for complete search history.

(56) References Cited

U.S. PATENT DOCUMENTS

| | | | |
|---|---|---|---|
| 6,985,524 B1 * | 1/2006 | Borchers ............ | G09B 21/008 345/549 |
| 7,124,375 B1 | 10/2006 | Steele et al. | |
| 2003/0137470 A1 | 7/2003 | Brown et al. | |

(Continued)

FOREIGN PATENT DOCUMENTS

| | | |
|---|---|---|
| JP | 4635572 B2 | 12/2010 |
| KR | 10-2006-0079404 A | 7/2006 |
| WO | 2005/013806 A2 | 2/2005 |

*Primary Examiner* — Jennifer Nguyen
(74) *Attorney, Agent, or Firm* — Cha & Reiter, LLC

(57) ABSTRACT

Electronic glasses having a display that correct for color blindness, and a method for operating the same. A user request for correction of color blindness is received. In response, a specific color is displayed, which is selected for correction of color blindness on the display. The display may be operated in a transparent state or in a display mode in which images are displayed. A color adjustment application may be executed to obtain color measurement result information for the particular user, where the specific color selected for correction of color blindness may be based on the measurement result information.

18 Claims, 8 Drawing Sheets

(56) References Cited

U.S. PATENT DOCUMENTS

| | | |
|---|---|---|
| 2006/0209258 A1* | 9/2006 | Nareppa ............... A61B 3/066 |
| | | 351/242 |
| 2009/0110271 A1 | 4/2009 | Chen et al. |
| 2011/0043644 A1 | 2/2011 | Munger et al. |
| 2011/0157180 A1 | 6/2011 | Burger et al. |
| 2012/0068913 A1 | 3/2012 | Bar-Zeev et al. |
| 2012/0147163 A1 | 6/2012 | Kaminsky |
| 2012/0299950 A1* | 11/2012 | Ali .................... G02B 27/0176 |
| | | 345/592 |
| 2013/0002660 A1* | 1/2013 | Chikazawa ........ H04N 13/0425 |
| | | 345/419 |
| 2013/0257849 A1* | 10/2013 | Doherty ............. H04N 13/0429 |
| | | 345/419 |
| 2013/0335435 A1* | 12/2013 | Ambrus .................. G06T 19/20 |
| | | 345/589 |
| 2015/0022773 A1* | 1/2015 | Kim ....................... G02C 7/101 |
| | | 351/44 |
| 2015/0149902 A1* | 5/2015 | Zavesky ............. G09B 21/008 |
| | | 715/716 |
| 2015/0169070 A1* | 6/2015 | Harp ....................... G06F 3/017 |
| | | 345/419 |
| 2015/0302773 A1* | 10/2015 | Stone .................. G02B 6/0035 |
| | | 348/63 |

* cited by examiner

FIG. 4
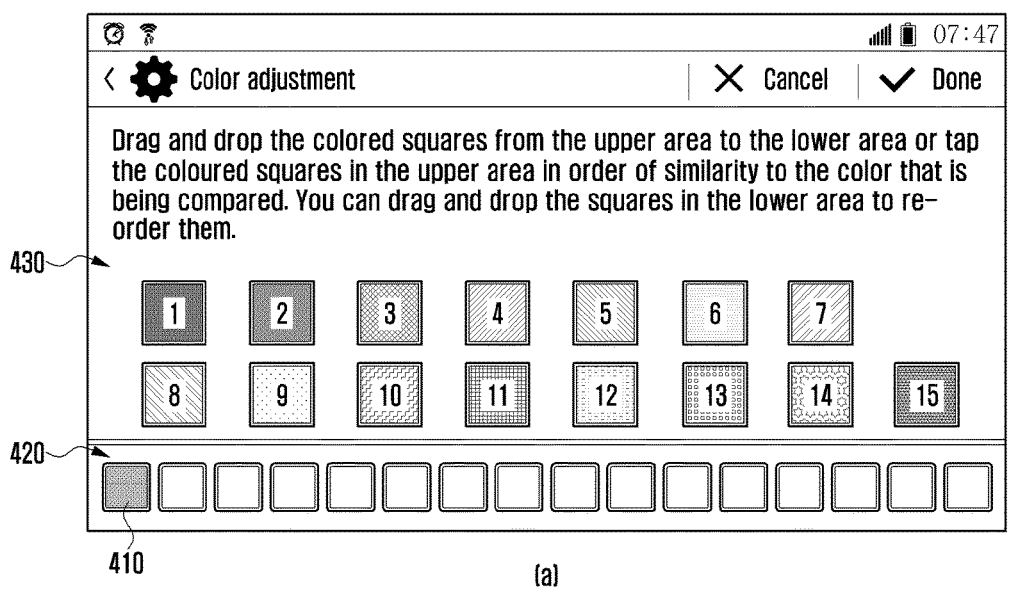
(a)
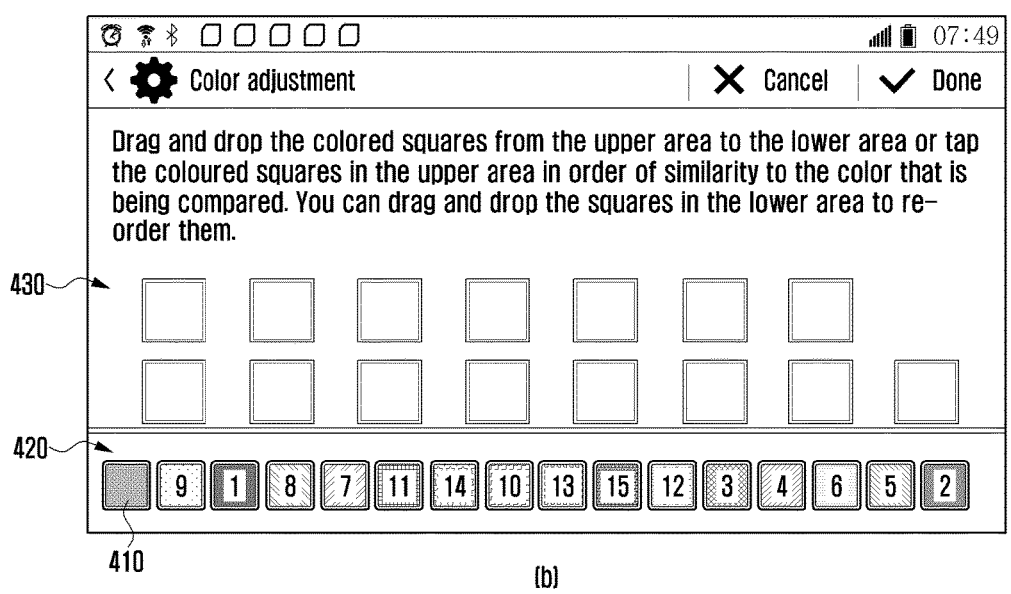
(b)

ELECTRONIC GLASSES AND METHOD FOR CORRECTING COLOR BLINDNESS

CLAIM OF PRIORITY

This application claims the benefit under 35 U.S.C. § 119(a) of a Korean patent application filed on Jan. 6, 2014 in the Korean Intellectual Property Office and assigned Serial No. 10-2014-0001457, the entire disclosure of which is hereby incorporated by reference.

TECHNICAL FIELD

Embodiments of the present disclosure relate to electronic glasses having a display and a method for operating the electronic glasses to correct color blindness.

BACKGROUND

Color blindness, or color vision deficiency, is the inability or decreased ability to see color, or perceive color differences, under normal lighting conditions. A partial inability to distinguish colors is referred to as color weakness. Color blindness is not medically curable, but special glasses and contact lenses have been developed to alleviate color blindness. Meanwhile, some recent electronic devices (not configured as wearable glasses) have the ability to correct color blindness through a technique known as a negative color. This technique involves binarization processing of converting a positive image, obtained by a camera, to a negative image and displaying the negative image on a screen so that a color weak or color blind user may view the screen with colors corrected for that user.

SUMMARY

Conventional glasses or contact lenses specially designed for correction of color blindness are inherently tinted with a specific color pre-selected for individualized correction. Therefore, a user who wears such glasses or contact lenses always views the surrounding environment with a changed color in a fixed manner.

Embodiments of the present disclosure beneficially provide electronic glasses and operating methods thereof which perform correction of color blindness on an as-needed basis. Embodiments provide glasses with dynamic color-correction capability. A color correction mode of the glasses may be switched on and off so that the user may selectively utilize the color correction mode.

According to embodiments of this disclosure, a method for operating electronic glasses having a display is provided. This method includes receiving a user request for correction of color blindness, and in response to the user request, displaying a specific color selected for correction of color blindness on the display. The display is then operated in a transparent state with the specific color displayed (e.g., the glasses are dynamically tinted) so as to correct for color blindness of the user.

According to embodiments of this disclosure, provided are electronic glasses that include a display; at least one of an input unit configured to recognize a user request and a communication module configured to receive a user request from an external device; and a processor configured to operate the electronic glasses in one of a display mode, a transparent mode, and a color blindness correction mode in response to the user request.

In the electronic glasses, the processor may be further configured to: in the display mode, control the transparent display to display images; in the transparent mode, control the display to enable passage of light therethrough; and in the color blindness correction mode, control the display to display thereon a specific color selected for correction of color blindness.

BRIEF DESCRIPTION OF THE DRAWINGS

FIG. 4 is a screenshot illustrating an execution image of a color adjustment application executed in an electronic device to correct color blindness in accordance with an embodiment of the present disclosure.

DETAILED DESCRIPTION

Figure 1:
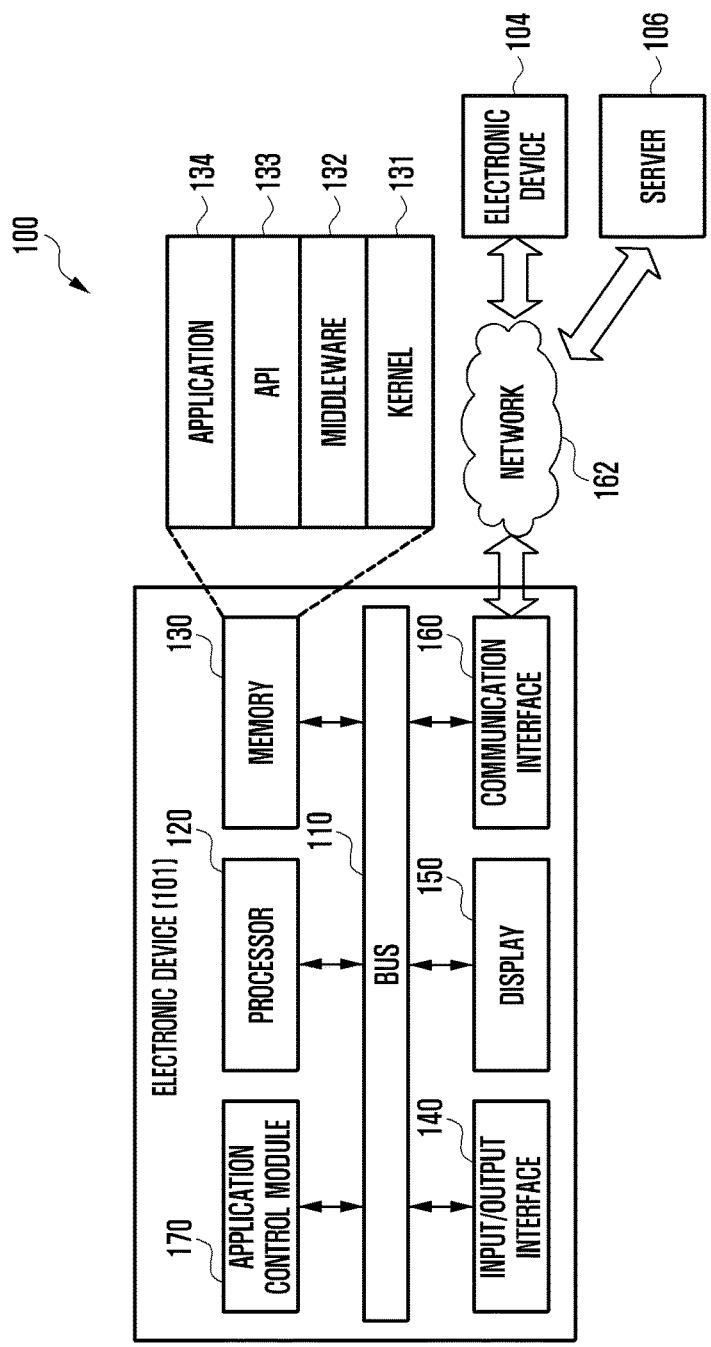
FIG. 1 is a block diagram illustrating a network environment including therein an electronic device in accordance with an embodiment of the present disclosure.

Hereinafter, the present disclosure will be described with reference to the accompanying drawings. The present disclosure may have various embodiments, and modifications and changes may be made therein. Therefore, the present invention will be described in detail with reference to particular embodiments shown in the accompanying drawings. However, it should be understood that there is no intent to limit the present disclosure to the particular forms, and the present disclosure should be construed to cover all modifications, equivalents, and/or alternatives falling within the spirit and scope of the present disclosure. In describing the drawings, similar elements are designated by similar reference numerals.

As used in the present disclosure, the expression "include" or "may include" refers to the existence of a corresponding function, operation, or constituent element, and does not limit one or more additional functions, operations, or constituent elements. Further, as used in the present disclosure, the term such as "include" or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

As used in the present disclosure, the expression "or" includes any or all combinations of words enumerated together. For example, the expression "A or B" may include A, may include B, or may include both A and B.

While expressions including ordinal numbers, such as "first" and "second", as used in the present disclosure may modify various constituent elements, such constituent elements are not limited by the above expressions. For example, the above expressions do not limit the sequence and/or importance of the corresponding constituent elements. The above expressions may be used merely for the purpose of distinguishing a constituent element from other constituent elements. For example, a first user device and a second user device indicate different user devices although both are user devices. For example, a first constituent element may be termed a second constituent element, and likewise a second constituent element may also be termed a first constituent element without departing from the scope of the present disclosure.

When a component is referred to as being "connected" or "accessed" to any other component, it should be understood that the component may be directly connected or accessed to the other component, but another new component may also be interposed between them. Contrarily, when a component is referred to as being "directly connected" or "directly accessed" to any other component, it should be understood that there is no new component between the component and the other component.

The terms as used in various embodiments of the present invention are merely for the purpose of describing particular embodiments and are not intended to limit the present disclosure. Singular forms are intended to include plural forms unless the context clearly indicates otherwise.

Unless defined otherwise, all terms used herein, including technical terms and scientific terms, have the same meaning as commonly understood by a person of ordinary skill in the art to which the present disclosure pertains. Such terms as those defined in a generally used dictionary are to be interpreted to have the meanings equal to the contextual meanings in the relevant field of art, and are not to be interpreted to have ideal or excessively formal meanings unless clearly defined in the present disclosure.

Herein, the term "color-blind" is used to refer to a person with any color-vision-deficiency. Herein, "correcting" a color-blind condition or like phrase refers to improving the ability of the person to see a colored object or to distinguish between objects of different colors.

In this disclosure, an electronic device may be a device that involves a communication function. For example, an electronic device may be a smart phone, a tablet PC (Personal Computer), a mobile phone, a video phone, an e-book reader, a desktop PC, a laptop PC, a netbook computer, a PDA (Personal Digital Assistant), a PMP (Portable Multimedia Player), an MP3 player, a portable medical device, a digital camera, or a wearable device (e.g., an HMD (Head-Mounted Device) such as electronic glasses, electronic clothes, an electronic bracelet, an electronic necklace, electronic tattoos, an electronic accessory, or a smart watch).

According to some embodiments, an electronic device may be a smart home appliance that involves a communication function. For example, an electronic device may be a TV, a DVD (Digital Video Disk) player, audio equipment, a refrigerator, an air conditioner, a vacuum cleaner, an oven, a microwave, a washing machine, an air cleaner, a set-top box, a TV box (e.g., Samsung HomeSync™, Apple TV™, Google TV™, etc.), a game console, an electronic dictionary, an electronic key, a camcorder, or an electronic picture frame.

According to some embodiments, an electronic device may be a medical device (e.g., MRA (Magnetic Resonance Angiography), MRI (Magnetic Resonance Imaging), CT (Computed Tomography), ultrasonography, etc.), a navigation device, a GPS (Global Positioning System) receiver, an EDR (Event Data Recorder), an FDR (Flight Data Recorder), a car infotainment device, electronic equipment for ship (e.g., a marine navigation system, a gyrocompass, etc.), avionics, security equipment, or an industrial or home robot.

According to some embodiments, an electronic device may be furniture or part of a building or construction having a communication function, an electronic board, an electronic signature receiving device, a projector, or various measuring instruments (e.g., a water meter, an electric meter, a gas meter, a wave meter, etc.). An electronic device disclosed herein may be one of the above-mentioned devices or any combination thereof. Further, the electronic device according to the present disclosure may be a flexible device. It is noted that the above-mentioned electronic devices are exemplary only and not to be considered as a limitation of this disclosure.

Hereinafter, an electronic device according to various embodiments of the present disclosure will be discussed with reference to the accompanying drawings. The term "a user" as used in various embodiments may refer to any person who uses an electronic device or any other device (e.g., an artificial intelligence electronic device) using an electronic device.

FIG. 1 is a block diagram illustrating a network environment 100 including therein an electronic device 101 in accordance with an embodiment of the present disclosure. Electronic device 101 may include, but not limited to, a bus 110, a processor 120, a memory 130, an input/output interface 140, a display 150, a communication interface 160, and an application control module 170.

The bus 110 may be a circuit designed for connecting the above-discussed elements and communicating data (e.g., a control message) between such elements.

The processor 120 may receive commands from the other elements (e.g., the memory 130, the input/output interface 140, the display 150, the communication interface 160, or the application control module 170, etc.) through the bus 110, interpret the received commands, and perform the arithmetic or data processing based on the interpreted commands.

The memory 130 may store therein commands or data received from or created at the processor 120 or other elements (e.g., the input/output interface 140, the display 150, the communication interface 160, or the application control module 170, etc.). The memory 130 may include programming modules such as a kernel 131, a middleware 132, an application programming interface (API) 133, and an application 134. Each of the programming modules may be composed of software, firmware, hardware, and any combination thereof.

The kernel 131 may control or manage system resources (e.g., the bus 110, the processor 120, or the memory 130, etc.) used for performing operations or functions of the other programming modules, e.g., the middleware 132, the API 133, or the application 134. Additionally, the kernel 131 may offer an interface that allows the middleware 132, the API 133 or the application 134 to access, control or manage individual elements of the electronic device 101.

The middleware 132 may perform intermediation by which the API 133 or the application 134 communicates with the kernel 131 to transmit or receive data. Additionally, in connection with task requests received from the applications 134, the middleware 132 may perform a control (e.g., scheduling or load balancing) for the task request by using technique such as assigning the priority for using a system resource of the electronic device 101 (e.g., the bus 110, the processor 120, or the memory 130, etc.) to at least one of the applications 134.

The API 133, which is an interface for allowing the application 134 to control a function provided by the kernel 131 or the middleware 132, may include, for example, at least one interface or function (e.g., a command) for a file control, a window control, an image processing, a text control, and the like.

According to embodiments, the application 134 may include an SMS/MMS application, an email application, a calendar application, an alarm application, a health care application (e.g., an application for measuring quantity of motion or blood sugar), an environment information application (e.g., an application for offering information about atmospheric pressure, humidity, or temperature, etc.), and the like. Additionally or alternatively, the application 134 may be an application associated with an exchange of information between the electronic device 101 and any external electronic device (e.g., an external electronic device 104). This type application may include a notification relay application for delivering specific information to an external electronic device, or a device management application for managing an external electronic device.

For example, the notification relay application may include a function to deliver notification information created at any other application of the electronic device 101 (e.g., the SMS/MMS application, the email application, the health care application, or the environment information application, etc.) to an external electronic device (e.g., the electronic device 104). Additionally or alternatively, the notification relay application may receive notification information from an external electronic device and offer it to a user. The device management application may manage (e.g., install, remove or update) a certain function (a turn-on/turn-off of an external electronic device (or some components thereof), or an adjustment of brightness (or resolution) of a display) of any external electronic device communicating with the electronic device 101, a certain application operating at such an external electronic device, or a certain service (e.g., a call service or a message service) offered by such an external electronic device.

According to embodiments, the application 134 may include a specific application specified depending on attributes (e.g., a type) of an external electronic device (e.g., the electronic device 104). For example, in case an external electronic device is an MP3 player, the application 134 may include a specific application associated with a play of music. Similarly, in case an external electronic device is a portable medical device, the application 134 may include a specific application associated with a health care. In an embodiment, the application 134 may include at least one of an application assigned to the electronic device 101 or an application received from an external electronic device (e.g., the server 106 or the electronic device 104).

The input/output interface 140 may deliver commands or data, entered by a user through an input/output unit (e.g., a sensor, a keyboard, or a touch screen), to the processor 120, the memory 130, the communication interface 160, or the application control module 170 via the bus 110. For example, the input/output interface 140 may offer data about a user's touch, entered through the touch screen, to the processor 120. Also, through the input/output unit (e.g., a speaker or a display), the input/output interface 140 may output commands or data, received from the processor 120, the memory 130, the communication interface 160, or the application control module 170 via the bus 110. For example, the input/output interface 140 may output voice data, processed through the processor 120, to a user through the speaker.

The display 150 may display thereon various types of information (e.g., multimedia data, text data, etc.) to a user.

The communication interface 160 may perform a communication between the electronic device 101 and any external electronic device (e.g., the electronic device 104 of the server 106). For example, the communication interface 160 may communicate with any external device by being connected with a network 162 through a wired or wireless communication. A wireless communication may include, but not limited to, at least one of WiFi (Wireless Fidelity), BT (Bluetooth), NFC (Near Field Communication), GPS (Global Positioning System), or a cellular communication (e.g., LTE, LTE-A, CDMA, WCDMA, UMTS, WiBro, or GSM, etc.). A wired communication may include, but not limited to, at least one of USB (Universal Serial Bus), HDMI (High Definition Multimedia Interface), RS-232 (Recommended Standard 232), or POTS (Plain Old Telephone Service).

According to an embodiment, the network 162 may be a communication network, which may include at least one of a computer network, an internet, an internet of things, or a telephone network. According to an embodiment, a protocol (e.g., transport layer protocol, data link layer protocol, or physical layer protocol) for a communication between the electronic device 101 and any external device may be supported by at least one of the application 134, the API 133, the middleware 132, the kernel 131, or the communication interface 160.

The application control module 170 may process at least part of information obtained from the other elements (e.g., the processor 120, the memory 130, the input/output interface 140, or the communication interface 160, etc.) and then offer it to a user in various ways. For example, the application control module 170 may recognize information about access components equipped in the electronic device 101, store such information in the memory 130, and execute the application 134 on the basis of such information. A further description about the application control module 170 will be given hereinafter through FIGS. 2 to 9.

Figure 2:
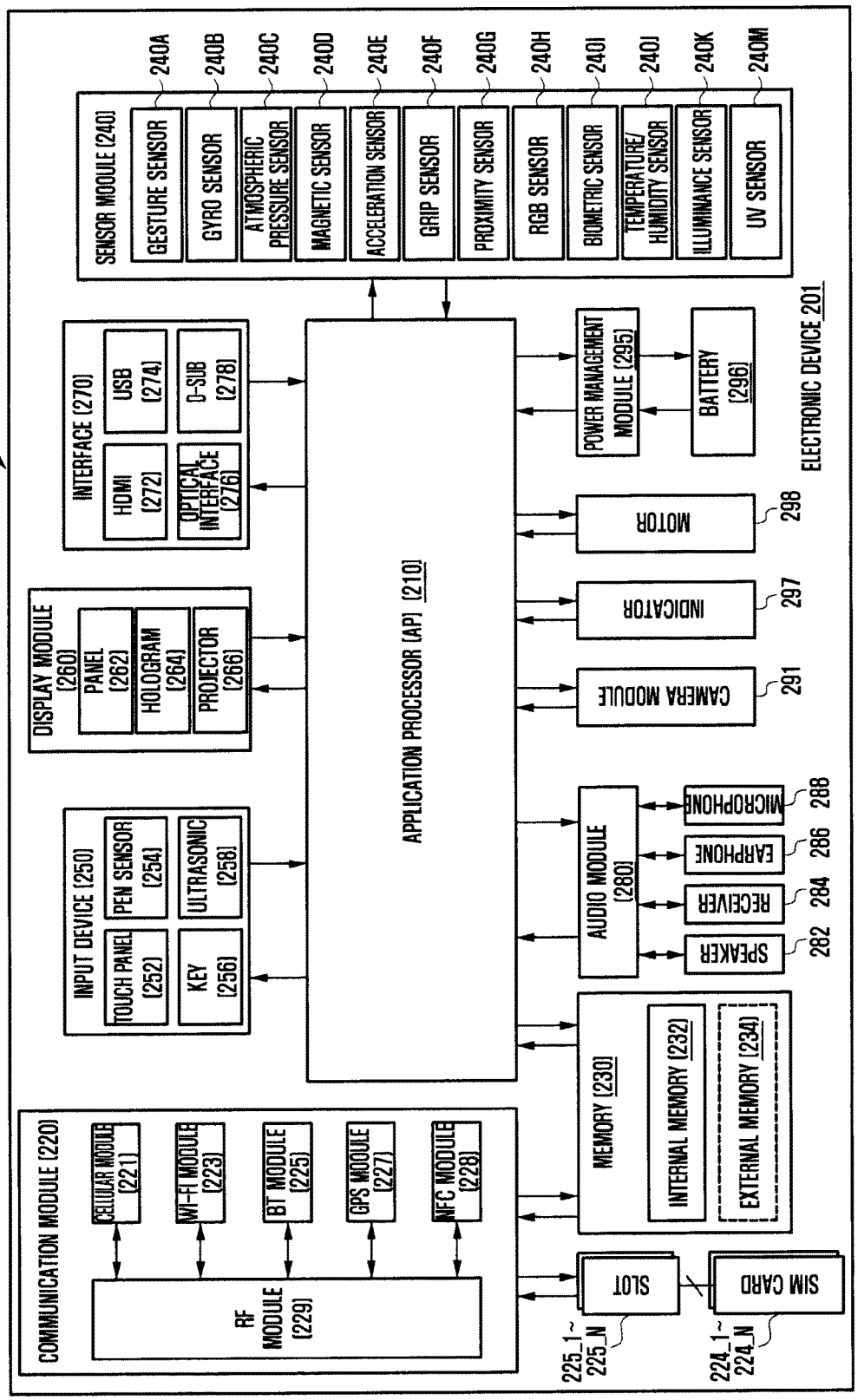
FIG. 2 is a block diagram illustrating an electronic device in accordance with an embodiment of the present disclosure.

FIG. 2 is a block diagram illustrating an electronic device 201 in accordance with an embodiment of the present disclosure. The electronic device 201 may form, for example, the whole or part of the electronic device 101 shown in FIG. 1. Electronic device 201 may include at least one application processor (AP) 210, a communication module 220, a subscriber identification module (SIM) card 224, a memory 230, a sensor module 240, an input unit 250, a display 260, an interface 270, an audio module 280, a camera module 291, a power management module 295, a battery 296, an indicator 297, and a motor 298.

The AP 210 may drive an operating system or applications, control a plurality of hardware or software components connected thereto, and also perform processing and operation for various data including multimedia data. The AP 210 may be formed of system-on-chip (SoC), for example. According to an embodiment, the AP 210 may further include a graphic processing unit (GPU) (not shown).

The communication module 220 (e.g., the communication interface 160) may perform data communication with any other electronic device (e.g., the electronic device 104 or the server 106) connected to the electronic device 200 (e.g., the electronic device 101) through the network. According to an embodiment, the communication module 220 may include therein a cellular module 221, a WiFi module 223, a BT module 225, a GPS module 227, an NFC module 228, and an RF (Radio Frequency) module 229.

The cellular module 221 may support a voice call, a video call, a message service, an internet service, or the like through a communication network (e.g., LTE, LTE-A, CDMA, WCDMA, UMTS, WiBro, or GSM, etc.). Additionally, the cellular module 221 may perform identification and authentication of the electronic device in the communication network, using the SIM card 224. According to an embodiment, the cellular module 221 may perform at least part of functions the AP 210 can provide. For example, the cellular module 221 may perform at least part of a multimedia control function.

According to an embodiment, the cellular module 221 may include a communication processor (CP). Additionally, the cellular module 221 may be formed of SoC, for example. Although some elements such as the cellular module 221 (e.g., the CP), the memory 230, or the power management module 295 are shown as separate elements being different from the AP 210 in FIG. 2, the AP 210 may be formed to have at least part (e.g., the cellular module 221) of the above elements in an embodiment.

According to an embodiment, the AP 210 or the cellular module 221 (e.g., the CP) may load commands or data, received from a nonvolatile memory connected thereto or from at least one of the other elements, into a volatile memory to process them. Additionally, the AP 210 or the cellular module 221 may store data, received from or created at one or more of the other elements, in the nonvolatile memory.

Each of the WiFi module 223, the BT module 225, the GPS module 227 and the NFC module 228 may include a processor for processing data transmitted or received therethrough. Although FIG. 2 shows the cellular module 221, the WiFi module 223, the BT module 225, the GPS module 227 and the NFC module 228 as different blocks, at least part of them may be contained in a single IC (Integrated Circuit) chip or a single IC package in an embodiment. For example, at least part (e.g., the CP corresponding to the cellular module 221 and a WiFi processor corresponding to the WiFi module 223) of respective processors corresponding to the cellular module 221, the WiFi module 223, the BT module 225, the GPS module 227 and the NFC module 228 may be formed as a single SoC.

The RF module 229 may transmit and receive data, e.g., RF signals or any other electric signals. Although not shown, the RF module 229 may include a transceiver, a PAM (Power Amp Module), a frequency filter, an LNA (Low Noise Amplifier), or the like. Also, the RF module 229 may include any component, e.g., a wire or a conductor, for transmission of electromagnetic waves in a free air space. Although FIG. 2 shows that the cellular module 221, the WiFi module 223, the BT module 225, the GPS module 227 and the NFC module 228 share the RF module 229, at least one of them may perform transmission and reception of RF signals through a separate RF module in an embodiment.

The SIM card 224_1 to 224_N may be a specific card formed of SIM and may be inserted into a slot 225_1 to 225_N formed at a certain place of the electronic device. The SIM card 224_1 to 224_N may contain therein an ICCID (Integrated Circuit Card IDentifier) or an IMSI (International Mobile Subscriber Identity).

The memory 230 (e.g., the memory 130) may include an internal memory 232 and an external memory 234. The internal memory 232 may include, for example, at least one of a volatile memory (e.g., DRAM (Dynamic RAM), SRAM (Static RAM), SDRAM (Synchronous DRAM), etc.) or a nonvolatile memory (e.g., OTPROM (One Time Programmable ROM), PROM (Programmable ROM), EPROM (Erasable and Programmable ROM), EEPROM (Electrically Erasable and Programmable ROM), mask ROM, flash ROM, NAND flash memory, NOR flash memory, etc.).

According to an embodiment, the internal memory 232 may have the form of an SSD (Solid State Drive). The external memory 234 may include a flash drive, e.g., CF (Compact Flash), SD (Secure Digital), Micro-SD (Micro Secure Digital), Mini-SD (Mini Secure Digital), xD (eXtreme Digital), memory stick, or the like. The external memory 234 may be functionally connected to the electronic device 200 through various interfaces. According to an embodiment, the electronic device 200 may further include a storage device or medium such as a hard drive.

The sensor module 240 may measure physical quantity or sense an operating status of the electronic device 200, and then convert measured or sensed information into electric signals. The sensor module 240 may include, for example, at least one of a gesture sensor 240A, a gyro sensor 240B, an atmospheric sensor 240C, a magnetic sensor 240D, an acceleration sensor 240E, a grip sensor 240F, a proximity sensor 240G, a color sensor 240H (e.g., RGB (Red, Green, Blue) sensor), a biometric sensor 240I, a temperature-humidity sensor 240J, an illumination sensor 240K, and a UV (ultraviolet) sensor 240M. Additionally or alternatively, the sensor module 240 may include, e.g., an E-nose sensor (not shown), an EMG (electromyography) sensor (not shown), an EEG (electroencephalogram) sensor (not shown), an ECG (electrocardiogram) sensor (not shown), an IR (infrared) sensor (not shown), an iris scan sensor (not shown), or a finger scan sensor (not shown). Also, the sensor module 240 may include a control circuit for controlling one or more sensors equipped therein.

The input unit 250 may include a touch panel 252, a digital pen sensor 254, a key 256, or an ultrasonic input unit 258. The touch panel 252 may recognize a touch input in a manner of capacitive type, resistive type, infrared type, or ultrasonic type. Also, the touch panel 252 may further include a control circuit. In case of a capacitive type, a physical contact or proximity may be recognized. The touch panel 252 may further include a tactile layer. In this case, the touch panel 252 may offer a tactile feedback to a user.

The digital pen sensor 254 may be formed in the same or similar manner as receiving a touch input or by using a separate recognition sheet. The key 256 may include, for example, a physical button, an optical key, or a keypad. The ultrasonic input unit 258 is a specific device capable of identifying data by sensing sound waves with a microphone 288 in the electronic device 200 through an input tool that generates ultrasonic signals, thus allowing wireless recognition. According to an embodiment, the electronic device 200 may receive a user input from any external device (e.g., a computer or a server) connected thereto through the communication module 220.

The display 260 (e.g., the display 150) may include a panel 262, a hologram 264, or a projector 266. The panel 262 may be, for example, LCD (Liquid Crystal Display), AM-OLED (Active Matrix Organic Light Emitting Diode), or the like. The panel 262 may have a flexible, transparent or wearable form. The panel 262 may be formed of a single module with the touch panel 252. The hologram 264 may show a stereoscopic image in the air using interference of light. The projector 266 may project an image onto a screen, which may be located at the inside or outside of the electronic device 200. According to an embodiment, the display 260 may further include a control circuit for controlling the panel 262, the hologram 264, and the projector 266.

The interface 270 may include, for example, an HDMI (High-Definition Multimedia Interface) 272, a USB (Universal Serial Bus) 274, an optical interface 276, or a D-sub (D-subminiature) 278. The interface 270 may be contained, for example, in the communication interface 160 shown in FIG. 1. Additionally or alternatively, the interface 270 may include, for example, an MHL (Mobile High-definition Link) interface, an SD (Secure Digital) card/MMC (MultiMedia Card) interface, or an IrDA (Infrared Data Association) interface.

The audio module 280 may perform a conversion between sounds and electric signals. At least part of the audio module 280 may be contained, for example, in the input/output interface 140 shown in FIG. 1. The audio module 280 may process sound information inputted or outputted through a speaker 282, a receiver 284, an earphone 286, or a microphone 288.

The camera module 291 is a device capable of obtaining still images and moving images. According to an embodiment, the camera module 291 may include at least one image sensor (e.g., a front sensor or a rear sensor), a lens (not shown), an ISP (Image Signal Processor, not shown), or a flash (e.g., LED or xenon lamp, not shown).

The power management module 295 may manage electric power of the electronic device 200. Although not shown, the power management module 295 may include, for example, a PMIC (Power Management Integrated Circuit), a charger IC, or a battery or fuel gauge.

The PMIC may be formed, for example, of an IC chip or SoC. Charging may be performed in a wired or wireless manner. The charger IC may charge a battery 296 and prevent overvoltage or overcurrent from a charger. According to an embodiment, the charger IC may have a charger IC used for at least one of wired and wireless charging types. A wireless charging type may include, for example, a magnetic resonance type, a magnetic induction type, or an electromagnetic type. Any additional circuit for a wireless charging may be further used such as a coil loop, a resonance circuit, or a rectifier.

The battery gauge may measure the residual amount of the battery 296 and a voltage, current or temperature in a charging process. The battery 296 may store or create electric power therein and supply electric power to the electronic device 200. The battery 296 may be, for example, a rechargeable battery or a solar battery.

The indicator 297 may show thereon a current status (e.g., a booting status, a message status, or a recharging status) of the electronic device 200 or of its part (e.g., the AP 210). The motor 298 may convert an electric signal into a mechanical vibration. Although not shown, the electronic device 200 may include a specific processor (e.g., GPU) for supporting a mobile TV. This processor may process media data that comply with standards of DMB (Digital Multimedia Broadcasting), DVB (Digital Video Broadcasting), or media flow.

Each of the above-discussed elements of the electronic device disclosed herein may be formed of one or more components, and its name may be varied according to the type of the electronic device. The electronic device disclosed herein may be formed of at least one of the above-discussed elements without some elements or with additional other elements. Some of the elements may be integrated into a single entity that still performs the same functions as those of such elements before integrated.

The term "module" used in this disclosure may refer to a certain unit that includes one of hardware, software and firmware or any combination thereof. The module may be interchangeably used with unit, logic, logical block, component, or circuit, for example. The module may be the minimum unit, or part thereof, which performs one or more particular functions. The module may be formed mechanically or electronically. For example, the module disclosed herein may include at least one of ASIC (Application-Specific Integrated Circuit) chip, FPGAs (Field-Programmable Gate Arrays), and programmable-logic device, which have been known or are to be developed.

Figure 3:
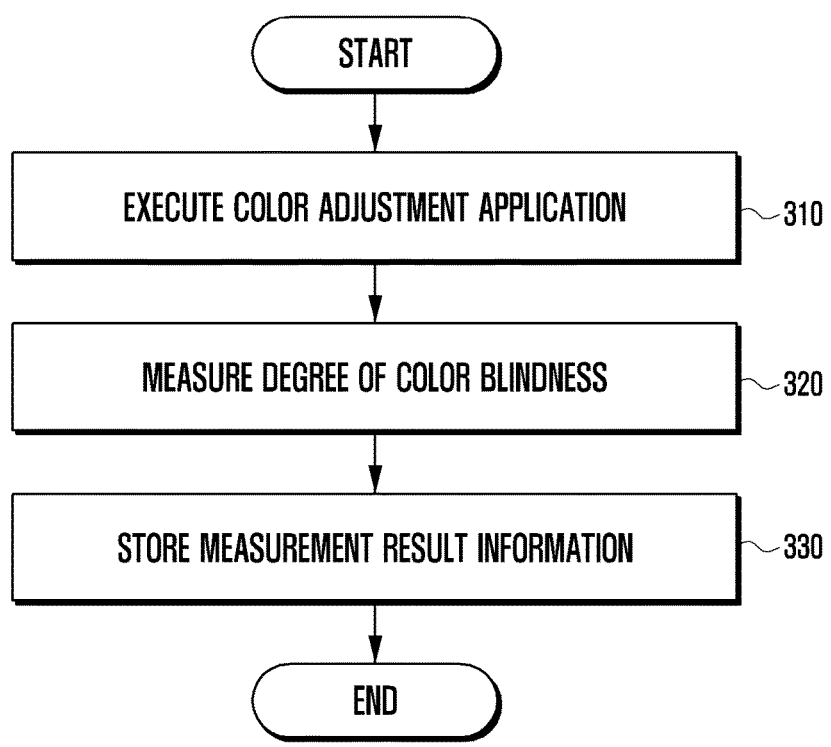
FIG. 3 is a flow diagram illustrating a method for testing a degree and type of color blindness in accordance with an embodiment of the present disclosure.

FIG. 3 is a flow diagram illustrating a method for testing the degree and type of color blindness in accordance with an embodiment of the present disclosure. FIG. 4 is a screenshot illustrating an execution image of a color adjustment application executed in an electronic device to correct color blindness in accordance with an embodiment of the present disclosure.

Referring collectively to FIGS. 3 and 4, the AP 210 of an electronic device (e.g., the electronic device 200) may receive a command for executing the color adjustment application from the input unit 250. At step 310, the AP 210 may execute a color adjustment application stored in the memory 230 in response to the command.

At step 320, the AP 210 may perform the measurement of the degree of color blindness in the color adjustment application. For example, the measurement of the degree of color blindness is as follows. AP 210 may control the display module 260 to display thereon an execution image, such as the screenshot (a) in FIG. 4. A first area 420 of the execution image may contain a reference object 410. The reference object 410 has a specific color of red, green or blue. Additionally, the second area 430 may contain a plurality of comparison target objects (labeled "1" through "15"). At least one of the comparison target objects has the same color as the reference object 410. The respective comparison target objects may each have a different color. Also, as shown, the comparison target objects may be numbered, for example, from one to fifteen. As illustrated in the screenshot, a user may be prompted to select the comparison target objects one by one in order of similarity in color to the reference object 410. If a user selects an object (e.g., having number '9') the touch panel 252 recognizes the user's tap input and then delivers the coordinates of the user input to the AP 210. In response, the AP 210 may place the selected object next to the reference object 410. Screenshot (b) in FIG. 4 shows an execution image after all of the comparison target objects have been selected. In the example, the first selection of the object '9' was followed in sequence by a selection of the object '1', etc.

At step 330, the AP 210 may store measurement result information in the memory 230. Alternatively or additionally, the AP 210 may control the communication module 220 to transmit the measurement result information to any external device (e.g., the electronic device 104 or the server 106), so that the measurement result information may be stored in the external device.

According to various embodiments, the measurement result information may have color placement information based on the reference object 410 as shown in screenshot (b) in FIG. 4. Using such color placement information, the AP 210 may determine color information for correcting color blindness. For example, the color information may be utilized to introduce a tint to the electronic glasses that is customized to the user. With such customized tinted glasses, the user may distinguish between different colored objects that would otherwise be indistinguishable.

When AP 210 determines the color information, it may be stored along with the measurement result information. Alternatively, the determination of color information may be performed at any external device (e.g., the server 106) that receives the measurement result information. This color information may then be transmitted to the electronic device 200 from the server 106, and the electronic device 200 may store the received color information in the memory 230.

Figure 5:
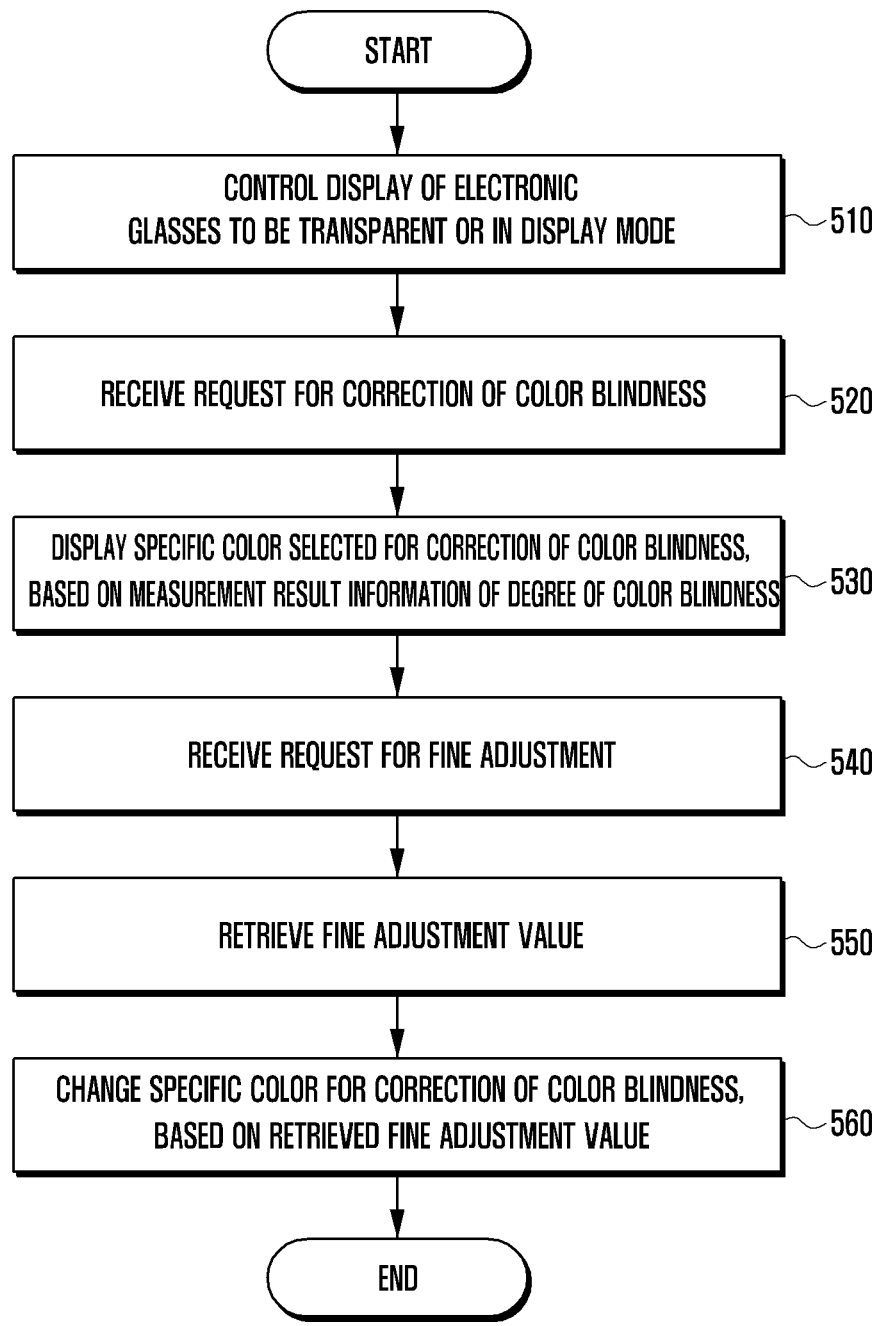
FIG. 5 is a flow diagram illustrating a method for correcting color blindness in accordance with an embodiment of the present disclosure.

FIG. 5 is a flow diagram illustrating a method for correcting color blindness in accordance with an embodiment of the present disclosure. The electronic device that implements this method may be electronic glasses. All or parts of elements discussed above and shown in FIG. 2 may be included in the electronic glasses.

Referring to FIG. 5, at step 510, the AP 210 of the electronic glasses may enable a display (e.g., the panel 262 having a flexible, transparent and wearable form) to be transparent. In other words, the AP 210 may operate the electronic glasses in a transparent mode. Herein, a transparent mode is a glasses mode usable by persons without color-deficient vision. That is, a transparent mode herein is a mode that allows light to at least partially pass through the glasses, and is not a mode for correcting color-deficient vision of a color-blind person. A transparent mode herein may be also called a non-colorblindness correction mode. However, the lenses of the glasses may be designed to correct vision in a conventional sense (e.g., focus), and/or may be designed as sunglasses to attenuate all wavelengths of light. In other words, a colorblind person may use the glasses in the transparent mode to correct his/her vision for improvement of focus and/or as conventional sunglasses.

In an alternative operation of step 510, the AP 210 may operate the electronic glasses in a display mode. The display mode is a mode in which the panel 262 may display thereon various visual objects (e.g., video, text, image, etc.). The display mode may have a color blindness correction option for a colorblind user, in which the colors of the displayed objects are modified for the colorblind user.

At step 520, the AP 210 may receive a request for correction of color blindness from the input unit 250. Such request for correction of color blindness is a request for initiating a colorblindness correction mode of the glasses. Alternatively, the AP 210 may receive the request for correction of color blindness from the microphone 288 or the earphone 286 through the audio module 280.

In response to the request for correction of color blindness, the AP 210 may operate the electronic glasses in a color blindness correction mode (i.e., a glasses mode for a color-blind person). An example of the color blindness correction mode is as follows. In response to the request for correction of color blindness, at step 530, the AP 210 may control the panel 262 to display thereon a specific color selected for correction of color blindness on the basis of the measurement result information of the degree and type of color blindness. For instance, the above-noted "determined color information" may be displayed on the display of the glasses so that at least a portion of the display is tinted to a certain hue, i.e., one or more colors of light are filtered out (attenuated) to some degree. By tinting the display in a customized way on the basis of the measurement result information, correction of color blindness is achieved for the particular colorblind individual. In the color blindness correction mode, the glasses may be partially transparent, i.e., the glasses are in a transparent state in which certain colors of light are attenuated, unless the user switches the glasses to a non-transparent display mode. (As noted above, the display mode may also include a color correction option.)

Additionally, at step 540, the AP 210 may receive a request for a fine adjustment from the input unit 250. Alternatively, the AP 210 may receive the request for a fine adjustment from the microphone 288 or the earphone 286 through the audio module 280. At step 550, the AP 210 may retrieve a fine adjustment value corresponding to the request for a fine adjustment from the memory 230. At step 560, the AP 210 may change a specific color for correction of color blindness, based on the retrieved fine adjustment value. Thus, the display tint may be slightly altered through the fine adjustment process.

According to various embodiments, the memory 230 may store therein various kinds of color information for correction of color blindness. Respective kinds of color information for correction of color blindness may be linked to identification information (e.g., name) about individual users. For example, the AP 210 may retrieve, from the memory 230, specific color information for correction of color blindness linked to a specific name entered through the input unit 250, and then control the panel 262 to display thereon a specific color according to the retrieved color information.

According to various embodiments, in response to a user request, the AP 210 may change an operating mode of the electronic glasses from a transparent mode to a display mode, from a transparent mode to a color blindness correction mode, from a display mode to a transparent mode, from a display mode to a color blindness correction mode, from a color blindness correction mode to a transparent mode, or from a color blindness correction mode to a display mode. Additionally, one or more operating modes of the electronic glasses may further include a fine adjustment mode that allows a user to finely adjust a specific color for correction of color blindness.

Figure 6:
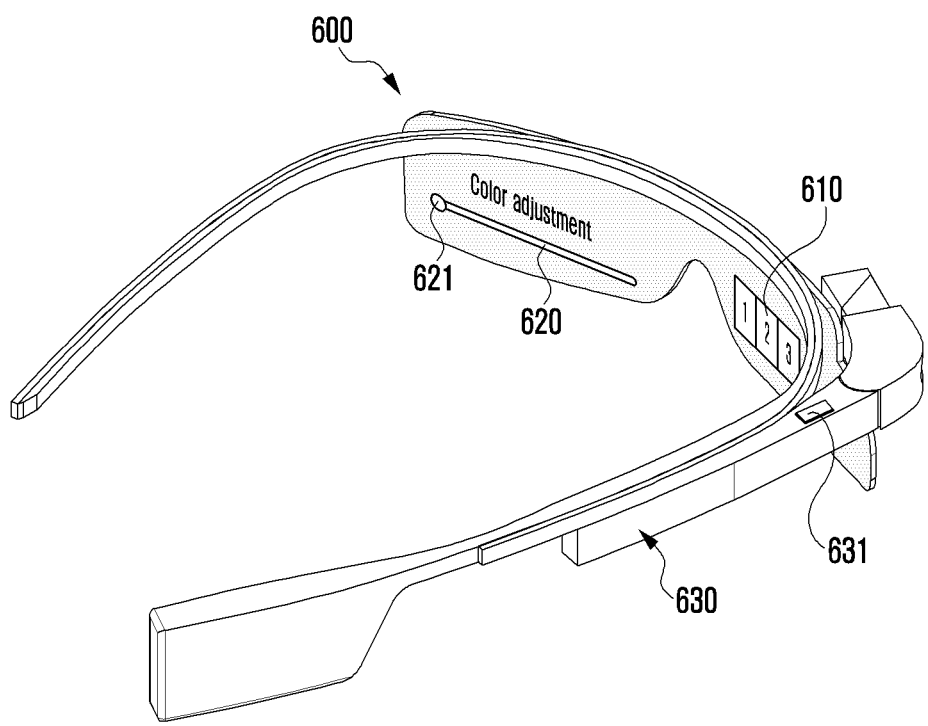
FIG. 6 is a perspective view illustrating electronic glasses operating in a fine adjustment mode in accordance with an embodiment of the present disclosure.

FIG. 6 is a perspective view illustrating electronic glasses, 600, operating in a fine adjustment mode in accordance with an embodiment of the present disclosure. Electronic glasses 600 may include all or parts of elements discussed above and shown in FIG. 2. The AP 210 of the electronic glasses 600 may operate the electronic glasses in a fine adjustment mode. An example of the fine adjustment mode is as follows. The AP 210 may control the panel 262 to display thereon a correction image 610 (to which a specific color for correction of color blindness is applied) and a fine adjustment guide bar 620. When a user presses a button 631 formed on a right sidepiece 630 (in this example) of the electronic glasses, the input unit 250 transmits key input information to the AP 210. Then the AP 210 may retrieve a fine adjustment value corresponding to the key input information from the memory 230, and change the specific color of the correction image 610, based on the retrieved fine adjustment value. Also, in response to the key input information, the AP 210 may move a pointer 621 of the fine adjustment guide bar 620 such that a user can perceive the degree of fine adjustment. Another press of button 631 (or a longer duration press) moves the pointer further. Pressing the button 631 also changes relative color among several regions of the correction image 610 (three in this example). If the user discerns that first, second and third regions are distinguished clearly in the correction image 610, the user may exit the fine adjustment mode by entering a voice command in the electronic glasses 600 or pressing an exit button (not shown). If the fine adjustment mode is exited, the operating mode of the electronic glasses 600 may return to the previous mode (e.g., a display mode, a transparent mode, or a color blindness correction mode).

Figure 7:
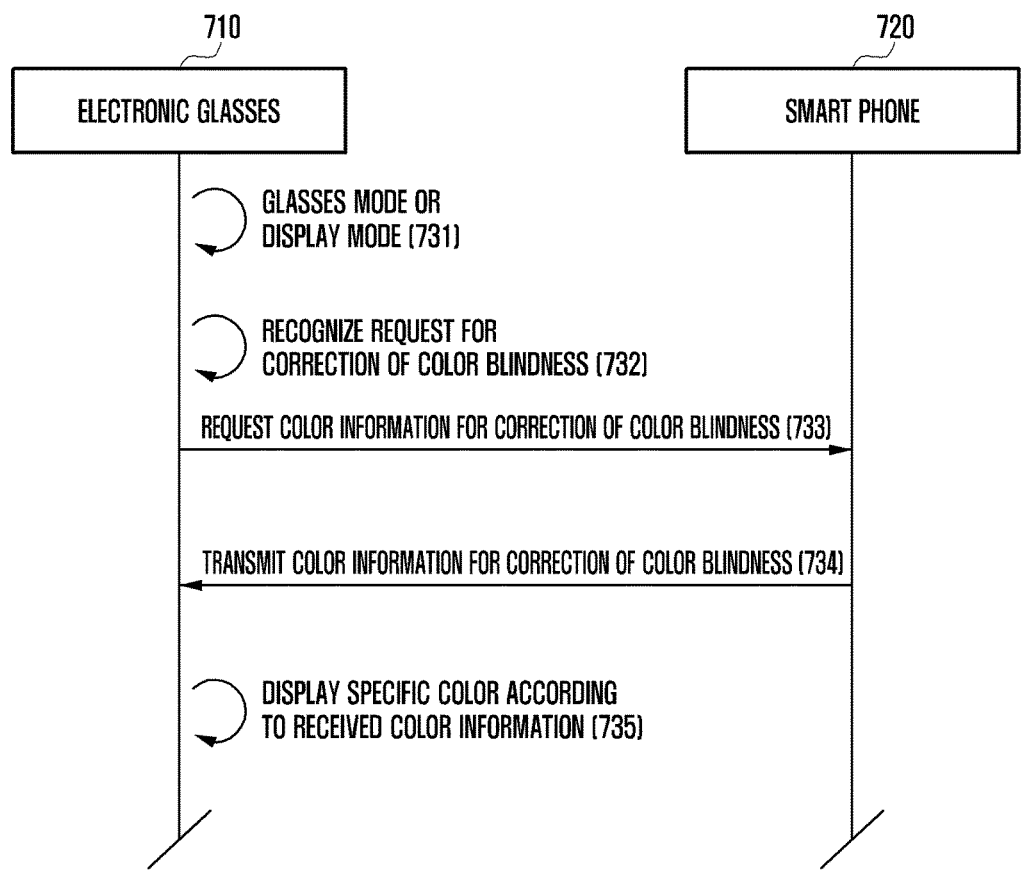
FIG. 7 is a flow diagram illustrating a method for correcting color blindness in accordance with another embodiment of the present disclosure.

FIG. 7 is a flow diagram illustrating a method for correcting color blindness in accordance with another embodiment of the present disclosure. This method may be performed using two electronic devices (e.g., electronic glasses 710 and a smart phone 720). Each of these electronic devices 710 and 720 may include all or parts of elements discussed above and shown in FIG. 2.

At step 731, the electronic glasses 710 may operate in a transparent mode or a display mode. At step 732, the electronic glasses 710 may recognize a request for correction of color blindness. At step 733, the electronic glasses 710 may transmit, to the smart phone 720, a request message for requesting color information to be used for correction of color blindness. Then, at step 734, the smart phone 720 may transmit, to the electronic glasses 710, a response message that contains color information for correction of color blindness. At step 735, the electronic glasses 710 may display thereon a specific color according to the received color information.

According to various embodiments, the electronic device that communicates with the electronic glasses 710 may be a certain device (e.g., the server 106) other than the smart phone 720. The electronic device (e.g., the server 106 or the smart phone 720) may store therein various kinds of color information for correction of color blindness according to individual users. For example, the electronic glasses 710 may transmit a request message to the server 106 or the smart phone 720. This request message may contain user identification information. In response to the request message, the server 106 or the smart phone 720 may retrieve, from a database thereof, color information for correction of color blindness corresponding to the user identification information and then transmit a response message containing the retrieved information to the electronic glasses 710.

Figure 8:
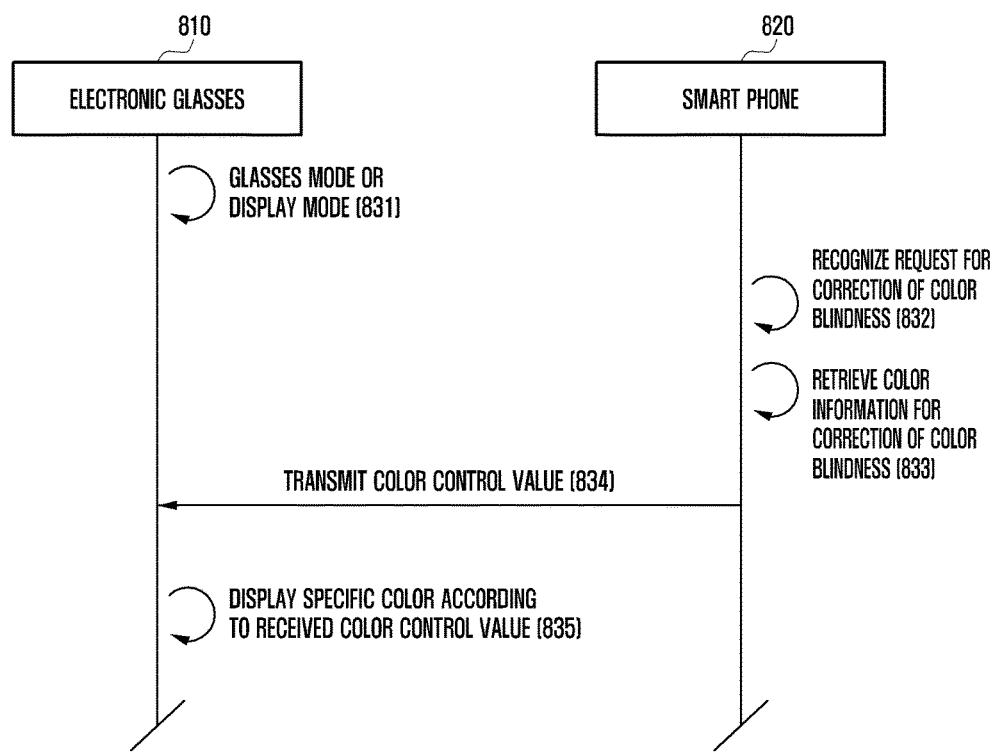
FIG. 8 is a flow diagram illustrating a method for correcting color blindness in accordance with still another embodiment of the present disclosure

FIG. 8 is a flow diagram illustrating a method for correcting color blindness in accordance with still another embodiment of the present disclosure. This method may be performed using two electronic devices (e.g., electronic glasses 810 and a smart phone 820). Each of these electronic devices 810 and 820 may include all or parts of elements discussed above and shown in FIG. 2.

Referring to FIG. 8, at step 831, the electronic glasses 810 may operate in a transparent mode or a display mode. At step 832, the smart phone 820 may recognize a request for correction of color blindness. In response to the request for correction of color blindness, at step 833, the smart phone 820 may retrieve, from a memory thereof or any external device, color information to be used for correction of color blindness. Then, at step 834, the smart phone 820 may transmit, to the electronic glasses 810, a color control value corresponding to the retrieved information. At step 835, the electronic glasses 810 may display thereon a specific color according to the received color control value.

As discussed hereinabove, electronic glasses and operating methods thereof in accordance with the disclosure may perform correction of color blindness on an as-needed basis, and may switch operating modes between a color blindness correction mode and a non-colorblindness correction mode. In this manner, a user may selectively utilize the color blindness correction mode. In addition, different users with different degrees/types of color vision deficiencies may each use the electronic glasses in a mode optimized for their own vision.

The above-discussed methods have been described herein with reference to flowchart illustrations of user interfaces, methods, and computer program products according to embodiments of the present disclosure. It will be understood that each block of the flowchart illustrations, and combinations of blocks in the flowchart illustrations, can be implemented by computer program instructions. These computer program instructions can be provided to a processor of a general purpose computer, special purpose computer, or other programmable data processing apparatus to produce a machine, such that the instructions, which are executed via the processor of the computer or other programmable data processing apparatus, create means for implementing the functions specified in the flowchart block or blocks. These computer program instructions may also be stored in a computer usable or computer-readable memory that can direct a computer or other programmable data processing apparatus to function in a particular manner, such that the instructions stored in the computer usable or computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that are executed on the computer or other programmable apparatus provide steps for implementing the functions specified in the flowchart block or blocks.

Moreover, each block of the flowchart illustrations may represent a module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

While this disclosure has been particularly shown and described with reference to exemplary embodiments thereof, it will be understood by those skilled in the art that various changes in form and details may be made therein without departing from the spirit and scope of this disclosure as defined by the appended claims.

What is claimed is:

1. A method for operating electronic glasses, the method comprising:
 receiving a user request for correction of color blindness;
 in response to the user request, displaying a specific color selected for correction of color blindness on a display of the electronic glasses, and operating the display in a partially transparent state with the specific color displayed so as to correct for color blindness of a user; and
 in response to a user request for fine adjustment, displaying a guide on the display to guide a user input for changing the specific color for correction of color blindness, wherein the guide includes at least two regions each displaying a different color, the at least two regions displayed concurrently with the guide, such that as the user input causes the specific color to change, a color contrast between the at least two regions increases.

2. The method of claim 1, further comprising:
 in response to the user request for correction of color blindness,
 retrieving color information for correction of color blindness from a memory of the electronic glasses; or transmitting a message for requesting color information for correction of color blindness to an external device,
wherein the displaying of the specific color includes displaying the specific color on the basis of the retrieved color information or the requested color information.

3. The method of claim 2, wherein the message contains user identification information.

4. The method of claim 1, wherein the user request for correction of color blindness is received from a button on the electronic glasses or a microphone of the electronic glasses.

5. The method of claim 1, wherein the request for correction of color blindness is received from an external device and contains a color control value, and
wherein the displaying of the specific color includes displaying the specific color corresponding to the color control value on the display.

6. The method of claim 1, wherein the user request is received while the electronic glasses operate in a display mode for displaying an image on the display or in a transparent mode without color blindness correction.

7. The method of claim 6, further comprising:
in response to a user request for exiting a mode for correction of color blindness, operating the electronic glasses in the transparent mode or the display mode.

8. The method of claim 1, further comprising, prior to receiving the user request for correction of color blindness, executing a color adjustment application that comprises:
displaying a reference object with a predetermined color;
displaying a plurality of comparison target objects;
prompting the user to select at least one of the comparison target objects that is perceived closest in color to the reference object, and receiving a user selection thereof; and
obtaining measurement result information based on the user selection,
wherein the specific color selected for correction of color blindness is based on the measurement result information.

9. The method of claim 8, wherein prompting the user to select at least one of the comparison target objects comprises prompting the user to select a plurality of the target objects one by one in order of similarity in color to the reference object.

10. Electronic glasses comprising:
a display;
at least one of an input unit configured to recognize a user request and a communication module configured to receive a user request from an external device; and
a processor configured to operate the electronic glasses in one of a display mode, a transparent mode without color blindness correction, a fine adjustment mode, and a color blindness correction mode in response to the user request,
wherein the processor is further configured to:
in the display mode, control the display to display images,
in the transparent mode, control the display to enable passage of light therethrough,
in the color blindness correction mode, control the display to display thereon a specific color selected for correction of color blindness, wherein the display operates in a partially transparent state, and
in the fine adjustment mode, display a guide on the display to guide a user input for changing the specific color for correction of color blindness in response to a request for fine adjustment received from the input unit or the communication module, wherein the guide includes at least two regions each displaying a different color, the at least two regions displayed concurrently with the guide, such that as the user input causes the specific color to change, a color contrast between the at least two regions increases.

11. The electronic glasses of claim 10, further comprising:
a memory configured to store therein color information for correction of color blindness.

12. The electronic glasses of claim 10, wherein the communication module is further configured to transmit a message, containing user identification information, for requesting color information for correction of color blindness to the external device, and further configured to receive the color information from the external device.

13. The electronic glasses of claim 12, wherein the external device is one of a smartphone or a server.

14. The electronic glasses of claim 10, further comprising:
a microphone,
wherein the processor is further configured to receive a request for correction of color blindness from the microphone.

15. The electronic glasses of claim 10, wherein the processor is further configured to change an operating mode of the electronic glasses from the color blindness correction mode to the transparent mode or the display mode in response to a user request for exiting the color blindness correction mode.

16. The electronic glasses of claim 10, wherein the processor is further configured to:
prior to receiving the user request for correction of color blindness, execute a color adjustment application that comprises:
displaying a reference object with a predetermined color;
displaying a plurality of comparison target objects;
prompting the user to select at least one of the comparison target objects that is perceived closest in color to the reference object, and receiving a user selection thereof; and
obtaining measurement result information based on the user selection,
wherein the specific color selected for correction of color blindness is based on the measurement result information.

17. The electronic glasses of claim 16, wherein prompting the user to select at least one of the comparison target objects comprises prompting the user to select a plurality of the target objects one by one in order of similarity in color to the reference object.

18. Electronic glasses comprising:
a display;
at least one of an input unit configured to recognize a user request and a communication module configured to receive a user request from an external device; and
a processor configured to:
operate the electronic glasses in a color blindness correction mode, in response to the user request, wherein in the color blindness correction mode, the display is operated in a partially transparent state and is controlled to display thereon a specific color selected for correction of color blindness, and
in response to a user request for fine adjustment, display a guide on the display to guide a user input for changing the specific color for correction of color blindness, wherein the guide includes at least two regions each displaying a different color, the at least two regions displayed concurrently with the guide, such that as the user input causes the specific color to change, a color contrast between the at least two regions increases.

\* \* \* \* \*